(12) United States Patent
Lacovara

(10) Patent No.: US 6,888,635 B2
(45) Date of Patent: May 3, 2005

(54) DETECTION METHOD AND APPARATUS

(75) Inventor: Philip Lacovara, Tucson, AZ (US)

(73) Assignee: Ambalux Corporation, Tucson, AZ (US)

(*) Notice: Subject to any disclaimer, the term of this patent is extended or adjusted under 35 U.S.C. 154(b) by 333 days.

(21) Appl. No.: 10/007,456

(22) Filed: Dec. 5, 2001

(65) Prior Publication Data

US 2002/0067483 A1 Jun. 6, 2002

Related U.S. Application Data

(60) Provisional application No. 60/256,500, filed on Dec. 5, 2000.

(51) Int. Cl.$^7$ .......................... G01N 21/84; G01N 21/00
(52) U.S. Cl. .......................... 356/431; 356/429; 356/73; 356/238.1
(58) Field of Search ................................ 356/429–431, 356/73, 237.1–241.6; 250/438.1, 559.01–559.37, 439.1

(56) References Cited

U.S. PATENT DOCUMENTS

| | | | |
|---|---|---|---|
| 3,633,037 A | 1/1972 | Langenbeck | 250/219 |
| 3,673,418 A | 6/1972 | Wiig | 250/219 |
| 3,891,324 A | 6/1975 | Davies | 356/156 |
| 4,071,899 A | 1/1978 | Holy | 364/561 |
| 4,160,913 A | 7/1979 | Brenholdt | 250/563 |
| 4,200,801 A | 4/1980 | Schuresko | 250/458.1 |
| 4,255,050 A | 3/1981 | Beckstein et al. | 356/238 |
| 4,414,476 A | 11/1983 | Maddox et al. | 250/559.37 |
| 4,467,207 A | 8/1984 | Lerner et al. | 250/459.1 |
| 4,484,079 A | 11/1984 | Betz et al. | 250/548 |
| 4,656,360 A | 4/1987 | Maddox et al. | 250/559.37 |
| 4,722,607 A | 2/1988 | Anselment et al. | 356/417 |
| 4,728,800 A | 3/1988 | Surka | 250/572 |
| 4,786,177 A | 11/1988 | Beckstein et al. | 356/429 |
| 4,890,924 A | 1/1990 | Beckstein | 356/429 |
| 4,894,891 A | 1/1990 | Beckstein | 26/51.4 |
| 4,899,425 A | 2/1990 | Epple | 26/51.4 |
| 4,945,252 A | 7/1990 | Lerner et al. | 250/548 |
| 4,984,896 A | 1/1991 | Flamig | 356/429 |
| 5,416,593 A | 5/1995 | Vercruysse | 356/429 |
| 6,027,820 A | 2/2000 | O'Hagan et al. | 428/543 |
| 6,111,651 A | 8/2000 | Shakespeare | 356/429 |
| 6,151,117 A | 11/2000 | Tuhro et al. | 356/375 |
| 6,380,547 B1 | 4/2002 | Gonzalez et al. | 250/458.1 |

FOREIGN PATENT DOCUMENTS

| | | |
|---|---|---|
| JP | 5-210063 | 8/1993 |
| WO | WO 95/22058 | 8/1995 |
| WO | WO 01/56525 A1 | 8/2001 |

Primary Examiner—Gregory J. Toatley, Jr.
Assistant Examiner—Amanda Merlino
(74) Attorney, Agent, or Firm—Lawrence R. Oremland PC

(57) ABSTRACT

A method and apparatus for detecting fiducial marking on a material are disclosed. The fiducial marking is characterized by the ability to absorb light in a first wavelength range and to fluoresce in a second wavelength range that is outside the first wavelength range. An excitation source is configured to direct light at the material in the first wavelength range, to cause the fiducial marking material absorb the light in the first wavelength range and to fluoresce in the second wavelength range. A detection device is located at a predetermined site and is configured to optically examine the material at the predetermined detection site, to determine whether fluorescence from the fiducial marking which is in the second wavelength range is detected at the predetermined detection site.

25 Claims, 3 Drawing Sheets

DETECTION METHOD AND APPARATUS

RELATED APPLICATION/CLAIM OF PRIORITY

This application is related to and claims priority from Provisional Application Ser. No. 60/256,500, filed Dec. 5, 2000.

TECHNICAL FIELD

The present invention relates to a method and apparatus which uses fluorescent detection to provide highly sensitive detection of fiducial (e.g., registration) markings at intended locations in (or on) a material. The invention is particularly useful in detecting fiducial markings in carpeting or other patterned materials, where defects in patterned components of the materials can affect the aesthetics, production and/or installation of the final product.

BACKGROUND

Many industrial processes entail the production of materials in a continuous fashion, such as the manufacture of carpet, vinyl sheet goods, roofing material, textiles, plastic sheeting, tiles, and even steel. Some of these materials may contain patterns that are introduced for aesthetic purposes, and whose regularity and consistency in both short and long length scales, along and across the continuous sheet, are extremely important for the value, utility and merchantability of the product. An example is patterned carpeting, where the straightness of the pattern and freedom from bowing, skewing and other pattern defects is essential to the aesthetics, and to the proper and efficient seaming and installation of the product. The introduction of fiducial markings that can be sensed by an automated system will provide the capability to provide real-time monitoring and potentially correction of patterns errors in materials such as carpeting and other sheet goods.

Patterned carpet is typically formed using fibers that are tufted, using a "tufting machine" into a woven fabric known as primary backing. The tufted fibers form the "face fiber" of the carpet and are principally responsible for the esthetics and performance of the product.

An example of tufted carpet is shown in FIG. 2. The pattern of the carpet is established by tufting different types or colors of fibers into different locations on the primary backing. Following tufting, the primary backing is "finished" by bonding the tufted primary backing to a heavier, coarse woven fabric known as secondary backing. Such a process is performed on a "finishing line." Once the carpet has been finished it is highly rigid composite structure and pattern errors cannot be corrected without expensive and time-consuming "power stretching" during the installation process. Thus, there is considerable impetus for the development of a method and device for sensing pattern errors in carpet and correcting said errors prior to finishing.

The present invention permits the introduction of fiducial marks during the manufacture of the carpet that are invisible to the consumer but are none-the-less visible to equipment during the manufacture of the carpet. Moreover, the present invention is particularly useful in detecting fiducial marks in carpeting or other patterned materials, where defects in patterned components of the materials can affect the aesthetics, production and/or installation of the final product.

SUMMARY OF THE PRESENT INVENTION

The present invention provides a new and useful optical method and apparatus for detecting pattern distortions even in the presence of interfering light sources, difficult to recognize patterns, varying patterns, as may occur as different types of carpet or other materials are produced continuously and sequentially along the same production line, and high clutter backgrounds which render pattern detection with conventional cameras and optical sensors unreliable. By exciting and detecting fluorescence of an intentionally introduced fluorescent material, or of a known native fluorescent material, the present invention is able to discriminate between desired fiducial marks and other characteristics of the material which are not desired to be tracked.

According to the present invention, the fiducial marking on the material is characterized by the ability to absorb light in a first wavelength range and to fluoresce in a second wavelength range that is outside the first wavelength range. An excitation source is configured to direct light at the material in the first wavelength range, to cause the fiducial marking material absorb the light in the first wavelength range and to fluoresce in the second wavelength range. A detection device is located at a predetermined site and is configured to optically examine the material at the predetermined detection site, to determine whether fluorescence from the fiducial marking which is in the second wavelength range is detected at the predetermined detection site.

The principles of the present invention are particularly useful in examining and detecting flaws in moving carpet material, at any of several points in the production of a carpet. Moreover, the principles of the present invention are particularly useful in detecting fiducial marks in carpeting or other patterned materials, where defects in patterned components of the materials can affect the aesthetics, production and/or installation of the final product.

In this application reference to "carpet material" means a component of the material used to form a carpet, e.g. primary backing, tufting, tufted carpet component, secondary backing, etc. Additionally, reference to an "intrinsic" component of material means a component normally used in the material, and an "extrinsic" component of a material means a component not normally used in forming the material, but added to the material for the purposes of the present invention. Still further, reference to an element or component being "provided with" or "provided in" a material means that the element or component is associated with the material, but is not intended to be specific to the manner in which the element or component is associated with the material. Thus, a fiducal marking being "provided with" or "provided in" a length of carpet material encompasses external application of the fiducial marking to the carpet material, incorporation of the fiducial marking material into the material which is used to form the carpet material, or any other form of association.

Further features of the present invention will become apparent from the following detailed description, taken with reference to the accompanying drawings.

DETAILED DESCRIPTION

As described above, the present invention is particularly usefully in detecting defects in the production of carpet, and its principles are described below in connection with the production of tufted carpet. However, it will be clear to those in the art that the principles of the present invention can be used in connection with the detection of defects in various other materials besides tufted carpet.

Figure 2:
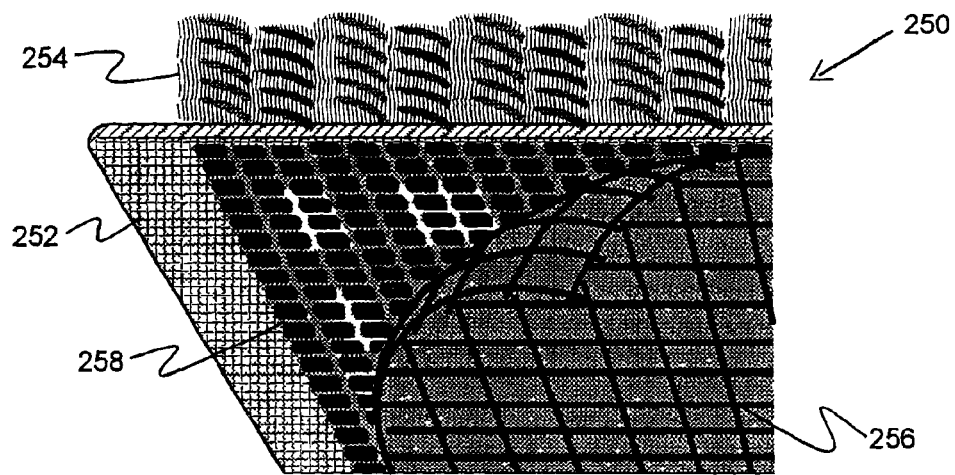
FIG. 2 is a schematic illustration of the components of tufted carpet, a patterned material with which the principles of the present invention can be practiced.

Initially, it is believed useful to describe, in general terms, known concepts for producing tufted carpet, and then to describe the principles of the present invention as they can be applied to sensing defects, or the absence of defects, in tufted carpet during its production. FIG. 2 schematically illustrates the components of a segment of tufted carpet 250. They include a primary backing 252, which is tufted with face pile 254, and then bonded to a secondary backing 256. Carpet pattern is established by tufting different yarns into the matrix of the primary backing 252 according to the desired pattern. Each of these yarns may have been pre-dyed to the desired color before tufting (via solution, stock or skein dyeing) so that the final pattern is visible after tufting, or the fibers may have been treated to accept different types of dyes during differential dyeing of the greige goods in a dye beck. In this process, fibers with different treatments will absorb different amounts of dye and thereby assume different colors. Fibers which are used in the primary backing, and fibers which form the tufting yarns, are often formed of extruded polymeric material, as is well known to those in the art.

The techniques for producing tufted carpet are well known. Initially, the primary backing material is provided in a predetermined configuration, and the yarns which form the face fiber are tufted into the primary backing, to produce a tufted carpet material. Following tufting (and where appropriate dyeing of the carpet material), the tufted primary backing is laminated to the secondary backing on a finishing line using an adhesive compound applied between the primary and secondary backing materials. In bonding the tufted primary backing to the secondary backing, it is conventional to use a rubbery adhesive known as SBR (styrene-butadeine rubber) latex. Mixed into the SBR latex are varying amounts of inorganic fillers to provide weight to the finished carpet to help it lie flat during installation, and to reduce the amount of the more expensive adhesive needed to fill in the voids in the composite. The application of the adhesive also serves to stabilize the yarn tufts at the rear of the primary backing and prevent them from pulling out from the front of the carpet. As can be seen from FIG. 2, the carpet 250 includes the tufted primary backing 252, the secondary backing 256, and the latex adhesive 258. In the finishing line, the carpet material is drawn through a drying oven using a tenter frame, which grabs the edges of the carpet and holds the carpet composite taught as it dries. The structures and operation of the drying oven and tenter frame are well known to those in the art and do not require further explanation.

Throughout the process of carpet manufacture there are a several opportunities for distortion of the carpet pattern. These distortions include bow, skew, and pattern elongation. A bow is distortion where the pattern is no longer arranged in lines perpendicular to the edges of the carpet, but is now curved (FIG. 4c schematically illustrates a carpet with a bow). In a skew distortion the pattern is still in straight, parallel lines, but it is no longer perpendicular to the edges of the carpet (FIG. 4b schematically illustrates a carpet with a skew distortion). In general, a distorted carpet may exhibit a combination of these distortions, perhaps including another type of distortion appearing within a foot or so of the edge of the carpet known as hook or dogleg.

Origins of bow, skew and other distortions during manufacture include:

Primary backing is not straight (instead it is bowed, skewed, stretched or hooked) as it enters the needle bar of the tufting machine due to incorrect alignment or tension or from poor quality of the backing roll;

Distortion during beck dyeing and re-rolling due to tension or temperature differentials or moisture absorption;

Misalignment during finishing due to speed, tension or alignment differences in the tenter frame or rollers.

These distortions must be corrected before the carpet composite dries, since the bond between the primary and secondary backing stiffens the carpet and makes it very difficult subsequently to correct errors. The present invention is designed to sense such errors at a point in the production process at which they may be most effectively corrected.

It is important to note that the same dyeing line or finishing line may process dozens of different types of carpets, with widely different mechanical properties, over the course of a production day. Indeed, different runs of carpet are sewn end-to-end on the finishing line to keep the line moving continuously, so that mechanical conditions on the line, such as tension or the density of the carpet, may be changing several times an hour as different carpeting moves through it.

Figure 4:
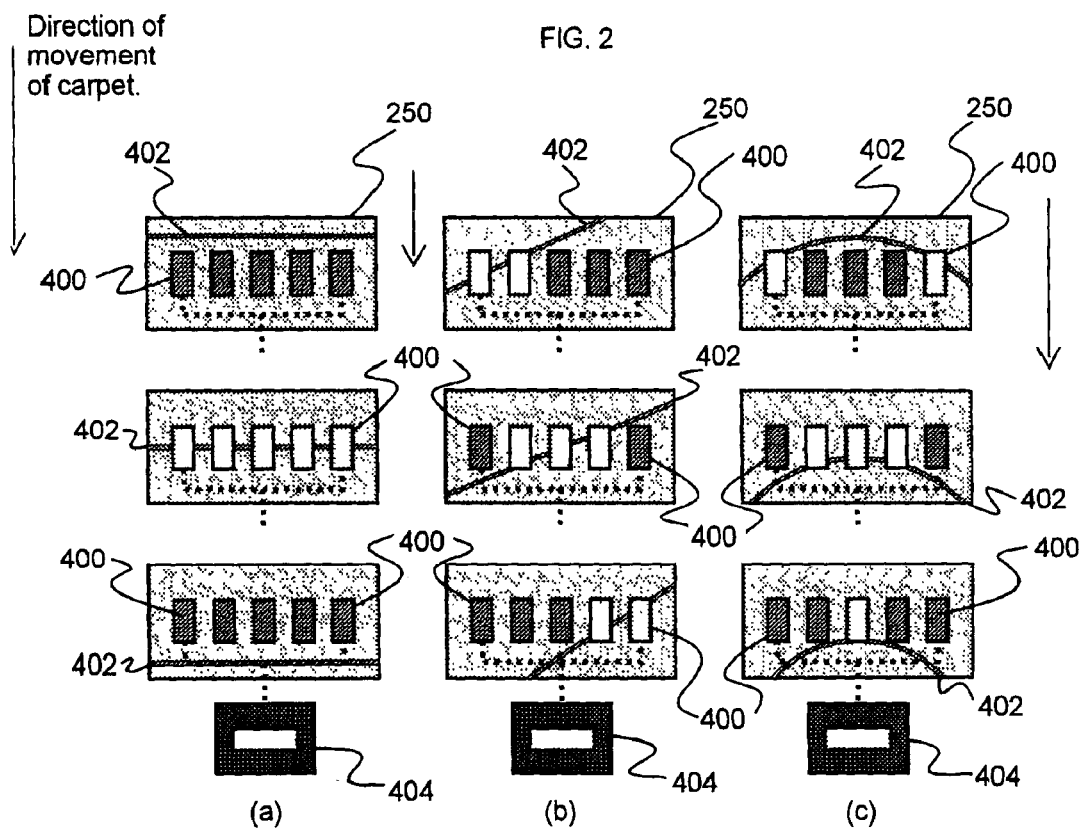
FIGS. 4a–4c schematically illustrate the manner in which a detection system according to the present invention would detect the presence or absence of defects in a moving length of carpet material.

The present invention provides a novel approach for sensing carpet distortions. Specifically, in one preferred form, shown in FIG. 4, a detection apparatus according to the present invention uses an array of sensors 400, each configured according to the principles of the invention, to detect a fiducial making, e.g. comprising a chemical that has been added in small concentrations to a pic-line 402, and forms an extrinsic component of the carpet. The detection apparatus may include several (5–7) sensors 400 arrayed along the weft of the fabric and connected with a computer 404 that receives the signals from the sensors, processes the signals and provides output that characterizes pattern errors in the carpet. The computer 404 can be, e.g., a conventional Pentium processor based computer. As illustrated in FIG. 4, the array of sensors 400 form an array of predetermined detection sites which extends transverse to the direction of movement of the carpet 250.

With the carpet pattern tufted straight in reference to the pic-line 402, the system detects any subsequent distortion by sensing the pic-line with and simply comparing the relative time that each sensor detects the pic-line. A sensor according to the present invention is able to reject the face fiber and backing fiber except for the pic-line 402, which it senses despite the intervening face fiber.

The chemical additive which is used in forming the pic-line 402 can be mixed into a polymer, extruded and woven into the primary backing. In that context, the additive forms an extrinsic component of the carpet material. Alternatively, the chemical additive can be applied on top of the primary backing material, e.g. by application to the surface of the primary backing with a spray, roller, brush or other application device.

Figure 1:
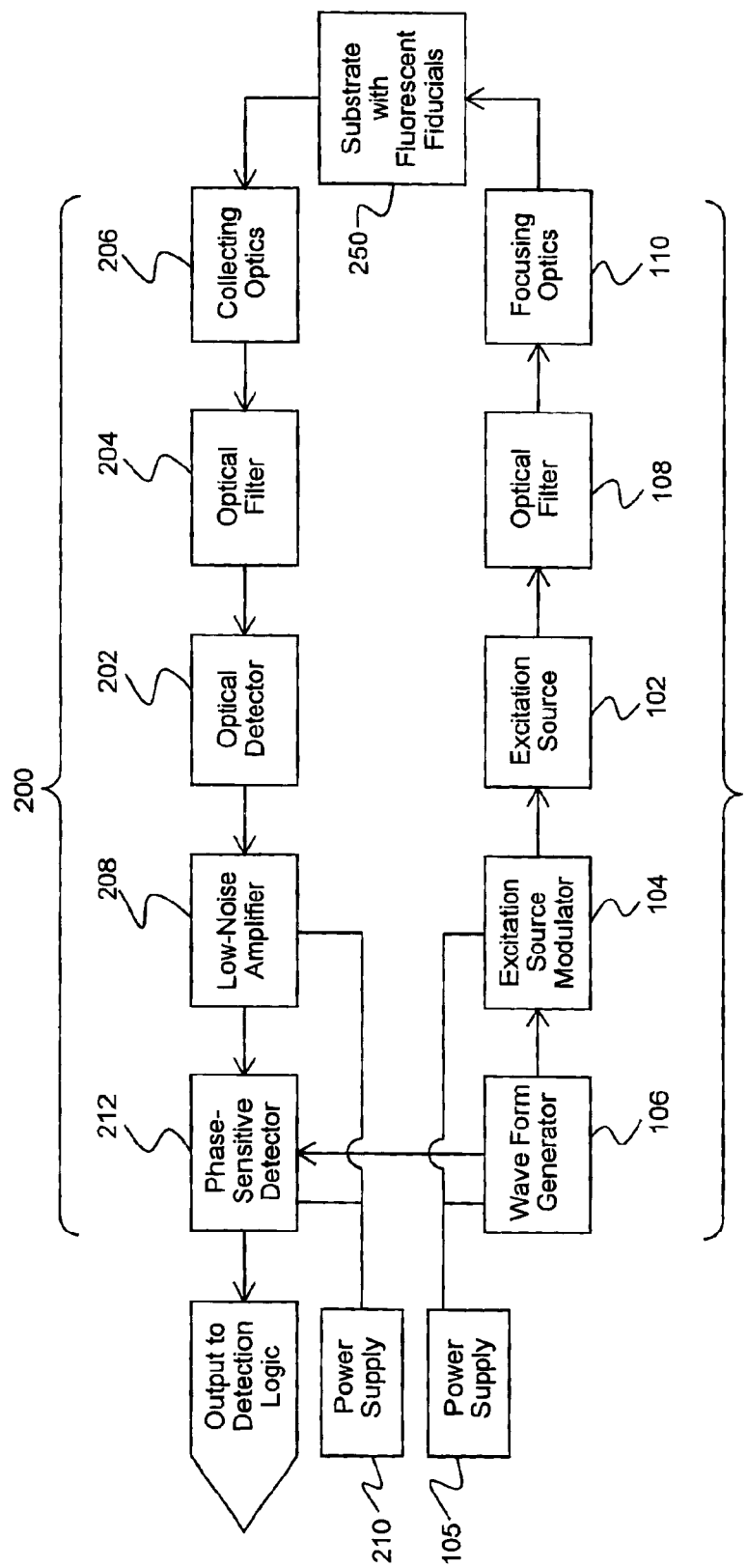
FIG. 1 is a schematic illustration of a system for detecting the presence or absence of fiducial markings provided in a material, according to the principles of the present invention.

A sensor 400 according to the present invention is schematically illustrated in FIG. 1. The sensor 400 includes a collimated, excitation light source 100, an efficient optical detector 200, signal processing and power conditioning.

Referring further to FIG. 1, the excitation source 100 is located at a predetermined site, and configured to direct light at the material 250 in the first wavelength range, to cause the fiducial marking material absorb the light in the first wavelength range and to fluoresce in the second wavelength range. A detection device 200 is located at the predetermined site and is configured to optically examine the material at the predetermined detection site, to determine whether fluorescence from the fiducial marking which is in the second wavelength range is detected at the predetermined detection site.

The optical excitation source 100 comprises a light source 102, and means of modulating said light source at a defined and controlled frequency and pattern such that signal-processing electronics can be used to discriminate between the fluorescent signal and background noise. Such signal processing electronics are discussed below. The light source may comprises a Light Emitting Diode (LED), e.g., a Nichia NSPB-500 LED, or a laser, which may be modulated directly by varying the input current according to the desired modulation scheme, or another type of light source which can be spectrally controlled and modulated using a mechanical chopper or other external modulating device so as to provide a beam of light which can be directed to excite fluorescence in a fluorescent material modulation pattern which facilitates signal processing.

For example, the excitation source 102 may be modulated by an excitation source modulator 104, e.g., a Metal oxide semiconductor field effect transistor (MOSFET), having a power supply 105. The modulator 104 is controlled by a wave form generator 106. The wave form generator 106, e.g., can use an integrated circuit and generate a frequency of 70 Hz to 100,000 Hz, typically 4,000 Hz.

The wavelength or spectral content or bandwidth of the excitation source 102 are chosen so as to maximize the excitation of fluorescence while minimizing any radiation at the wavelength or wavelength band of the fluorescent emission. For example, a blue LED which emits light preferentially near 455 nm may be used to excite fluorescence from a material which emits fluorescence near 600 nm. For circumstances where blue light excites undesired fluorescence from regions of the face fiber of the carpet or on some other substrate that is being processed, the wavelength or spectral content of the excitation source will, in general, be more useful in the red or the near-infrared spectral regions, such as 650, 750, 780 or 850 nm. At these wavelengths the intrinsic fluorescence of blue and other colored dyes used in the manufacture of carpet have relatively weak absorption and thereby weak excitation. Accordingly, operation at these red and infrared wavelengths can decrease interference from fluorescence of the face fiber and increase the contrast of the fiducial marks.

The excitation source 100 may include optical filters 108 (e.g., a Schott Red blocking filter) which use absorption or reflection or dispersive elements such as diffraction gratings, prisms or holographic elements to transmit light at the excitation wavelength or wavelengths and reject light at or near the fluorescence wavelength. Such optical filters may, in general, not be required when the excitation source is a laser, since the output of a laser is usually highly monochromatic. The optical excitation source may also include lenses, mirrors or other optics 110 (e.g., a 50 mm achromat lens) which direct and focus the excitation light onto the surface of the material 112 with a spot size which establishes the desired spatial resolution of the fiducials, and which matches the optical properties of the detection system 200. In some cases, the optical excitation sources may be located remotely from the desired monitoring location and the excitation light may be conducted from the excitation source to the monitoring location using a fiber-optic cable.

When the present invention is used in the manufacture of carpet and the sensor is employed such that it is viewing the front (face-fiber side) of the carpet, said focusing is important for directing as much as possible of the excitation light into the carpet between the face fibers, thereby allowing the maximum amount of excitation light to reach the fiducial marks in the backing and maximizing the sensitivity of the sensor. In general, when used with carpet or other materials wherein the fiducial marks are behind the surface of part of the material, the excitation and detection optics will be arranged such that they are collinear and mainly coaxial. In such a way, properly implemented through choice of optical components and their arrangement, the maximum amount of excitation light will be delivered to the fiducial marks, and the maximum amount of fluorescent light emitted by the fiducial marks will be captured by the detection optics. In addition, the coaxial arrangement may also reduce the amount of interfering light caused by residual fluorescence of the face fibers.

The fluorescence detector 200 comprises an optical detector 202, such as a semiconductor photodiode or a photomultiplier tube, and a means of transmitting the fluorescence wavelength or wavelengths and rejecting the excitation wavelength. Such means may include optical filters 204 (e.g., a Schott BG-610 colored glass filter and an Edmond Scientific 650 nm band pass filter) which use absorption or reflection or dispersive elements such as diffraction gratings, prisms or holographic elements to transmit light at the fluorescence wavelength or wavelengths and reject light at or near the excitation wavelength. The fluorescence detector also includes lenses, mirrors or other optics 206 (e.g., a 75 mm F/1 Fresnel lens and a 25 mm achromat lens) which direct and focus the fluorescent light from the surface of the substrate and matches the optical properties of the detection system. In some cases, the fluorescence detector may be located remotely from the desired monitoring location and the fluorescent light collected by the aforementioned lenses, mirrors or other optics 206 may be conducted from the monitoring location to the fluorescence detector using a fiber-optic cable.

The fluorescence detector will typically include a low-noise amplifier 208, either integral with the detector or connected electrically to its output (e.g., the optical detector and amplifier can be a Thor Labs silicon detector PDA-55 with integrated amplifier), to increase the electrical signal which results from the optical detection of the fluorescence. The design of such low-noise amplifiers, such as transimpedance amplifiers, is well now to those schooled in the art. The amplifier has a power supply 210.

Even with spectral selection as described above, the optical signal and the accompanying electrical output from the fluorescence detector may be dominated by background noise of optical and electrical origin. The desired fluorescence signal may be detected within the noisy background using phase-sensitive or lockin detection, wherein the signal and noise are provided to an analog mixer and demodulator which is synchronized with the modulation of the excitation source, or, alternatively, sampled by an analog-to-digital converter of sufficient resolution and bandwidth to sense the small difference between the signal when the excitation source is on and when it is off. As an example, a phase sensitive detector 212 (e.g., a Scitec Model 430) can be synchronized with the modulation of the excitation source 102, to demodulate the signal from the fluorescence detector and thereby sense the small difference between the signal when the excitation source is on and when it is off. Thus, the background noise can be averaged and subtracted from the actual fluorescence signal and the sensitivity of detection can be increased by several orders of magnitude. Similar performance can be implemented wholly in software using a computer with a high-resolution analog-to-digital converter.

In operation, the excitation and detection device would be located at a predetermined site, and the material carrying the fiducial marking would move past the predetermined site. When the material is a length of carpet for example, the fiducial markings would comprise, e.g., patterns extending widthwise across the length of carpet at intended locations on the carpet. Moreover, the detection device could comprise a series of detectors, of the type described herein, located at predetermined sites relative to the width of the carpet. The detectors can be configured such that if the patterns are where they should be on the carpet, all detectors should detect the presence of the predetermined patterns as the patterns move past the detectors. On the other hand, if only part of the detectors detect the patterns, as the carpet moves past the detectors, that would indicate the patterns are not where they should be, and an appropriate signal can be generated. Thus, FIG. 4(*a*) the pic-line 402 is straight and would be detected by all of the sensors at the same time, indicating the carpet is now bowed or skewed. In FIGS. 4(*b*) and 4(*c*), the pic-line 402 will be detected by different sensors at different times, indicating the carpet is skewed (FIG. 4(*b*)) or bowed (FIG. 4(*c*)).

Figure 3:
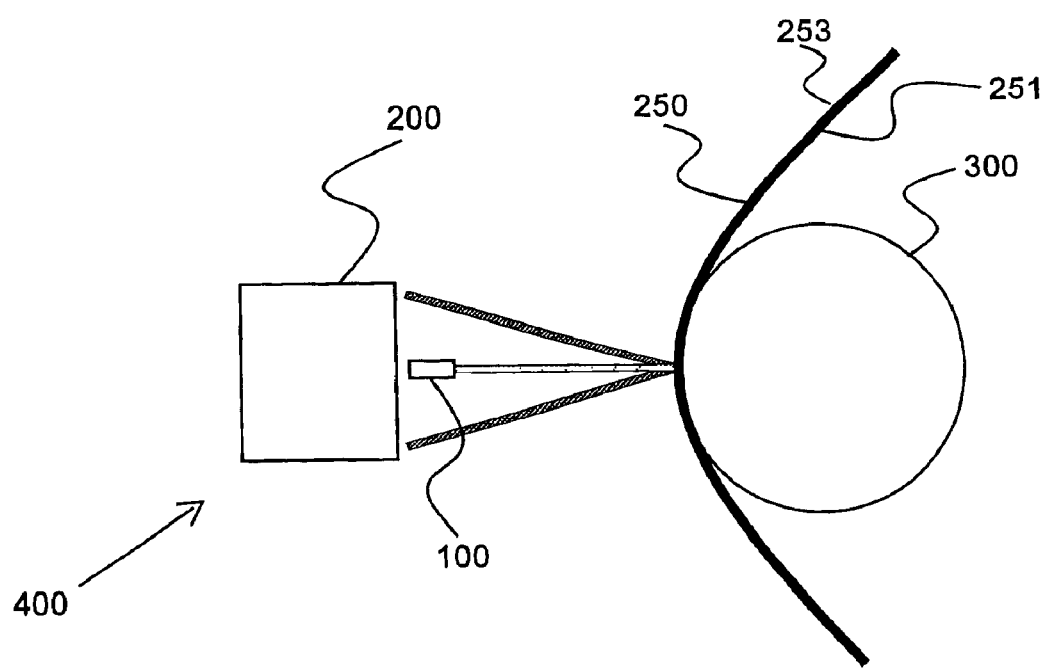
FIG. 3 is a schematic illustration of the location of a detection system according to the present invention, in relation to a length of carpet material passing over a roller.

The sensitivity of the invention may also be enhanced by positioning a sensor at a location wherein the carpet 250 passes over a roller 300 (FIG. 3), such that the face fibers spread, allowing greater visibility of the primary backing. The backside 251 of the carpet is on, or in immediate proximity to the roller 300, and the front side 253 of the carpet faces the sensor 400. Locations for such rollers and the sensors associated with the rollers are plentiful on carpet finishing lines, after the carpet has been tufted. For example, in a finishing line, the rollers and sensors can be located after the latex applicator and before the oven of the finishing line. Moreover, the rollers and sensors can be located after the oven, where cooling of the carpet begins. Additionally, the rollers can be located at the end of the finishing line. Alternatively, the tufting equipment generally includes rollers, so the roller and sensor arrangement of FIG. 3 can also be incorporated in the tufting equipment.

While most applications of the present invention will involve sensing through the front side of the carpet, the apparatus of the present invention can also be configured to sense the pic-line through the backside of the carpet. For example, the face fiber of the carpet typically extends away from the front side of the primary backing and toward the front side of the carpet (in FIG. 3, the front side of the carpet is shown at 253). If the latex adhesive layer is relatively thin, or if the adhesive between the primary and secondary backings comprises a clear thermoplastic adhesive or another relatively transmissive adhesive, the pic-line can be sensed through the backside of the carpet with the apparatus of the present invention, by directing the excitation beam at the backside of the primary backing.

In the practice of the present invention, the following additional points should be noted:

a. The invention uses fluorescent detection of a fluorescent substance in order to provide clutter rejection for the purpose of detecting fiducial markings.

b. The invention can use, e.g., native fluorescence from a pic line formed by a portion of the carpet material (i.e. an intrinsic material), or fluorescence from substance(s) which can be intentionally introduced into the material (i.e. an extrinsic material). For example, when the material is a carpet, the fluorescence substance could comprise fluorescent dye which withstands processing at high temperature (e.g., 550° F.), has absorption in the blue green wavelength range and emission widely separated (non overlapping the absorption range) in the yellow red wavelength range. An example of such a substance is Exalite 598 manufactured by Exciton Chemical Company, located in Ohio. A similar substance, having absorption in the red wavelength range and emission in the infrared wavelength range, is Exalite 648 by the same manufacturer.

c. Where the fiducial marking is introduced as an extrinsic component of a carpet, the extrinsic fiducial marking and the excitation source are characterized such that fluorescence is excited in the extrinsic fiducial marking but not in the intrinsic components of the carpet. Moreover, the detection device is configured to detect fluorescence in a predetermined wavelength range that is determined by the excitation source and extrinsic component of the carpet, and which substantially excludes fluorescence from intrinsic components of the carpet material.

d. The invention contemplates, e.g., introducing the fluorescent substance into a polymer for the purpose of automated detection, or coating polymer pellets with the fluorescent substance prior to heating and extrusion. In addition, the invention contemplates introducing fluorescent substance into a polymer by mixing a concentrated form of the fluorescent substance with the polymer prior to heating and extrusion.

e. The invention contemplates, besides, e.g., an LED or laser, an incandescent or gas-discharge lamp as the excitation source for fluorescence.

Accordingly, the foregoing description provides a method and apparatus which uses fluorescent detection to provide highly sensitive detection of fiducial (e.g., registration) markings at intended locations in (or on) a material. While the invention is described above in connection with detection of fiducial markings in carpeting, it will be clear to those in the art that its principles can be applied to detection of defects in other patterned materials, where defects in patterned components of the materials can affect the aesthetics, production and/or installation of the final product.

What is claimed is:

1. A method for detecting fiducial marking in a tufted carpet material, comprising the steps of a. providing tufted carpet material with at least one fiducial marking, the fiducial marking being in a configuration designed to be related to the pattern of the tufted carpet and characterized by the ability to absorb light in a first wavelength range and to fluoresce in a second wavelength range that is at least partially outside the first wavelength range, b. directing light at the tufted carpet material in the first wavelength range, to cause the fiducial marking material to absorb the light in the first wavelength range and to fluoresce in the second wavelength range, and c. optically examining the tufted carpet material at a predetermined detection site relative to the tufted carpet material, to determine whether fluorescence from the fiducial marking which is in the second wavelength range is detected at the predetermined detection site and to provide output related to the configuration of the fiducial marking.

2. A method as set forth in claim 1, wherein the fiducial marking is provided as an intrinsic component of the tufted carpet material.

3. A method as set forth in claim 1, wherein the fiducial marking is provided as an extrinsic component of the tufted carpet material.

4. A method as set forth in claim 3, wherein the extrinsic fiducial marking and the excitation source are characterized such that fluorescence is excited in the extrinsic fiducial marking but not in the intrinsic components of the tufted carpet material.

5. A method as set forth in any of claims 1–4, wherein the tufted carpet material includes a primary backing, and the fiducial marking is provided in the primary backing.

6. A method as set forth in claim 5, wherein the fiducial marking is provided on the surface of the primary backing.

7. A method as set forth in claim 5, wherein the primary backing is at least partially woven from an extruded polymeric material, and the fiducial marking is introduced into the polymeric material.

8. A method as set forth in claim 1, wherein the tufted carpet material includes face fiber that provides part of the pattern of the tufted carpet, and the fiducial marking is provided in the face fiber.

9. A method as set forth in claim 8, wherein the fiducial marking is provided on the surface of the face fiber.

10. A method as set forth in claim 8, wherein the face fiber is at least partially formed from an extruded polymeric fiber, and the fiducial marking is introduced into the polymeric material forming the polymeric fiber.

11. A method as set forth in claim 5, wherein the tufted carpet material comprises tufted carpet material having face fiber that provides the pattern of the tufted carpet, and wherein the fiducial marking is provided in the face fiber.

12. A method of detecting fiducial markings provided in a moving carpet material, the fiducial markings in a configuration designed to be related to the pattern of the carpet and characterized by the ability to absorb light in a first wavelength range and to fluoresce in a second wavelength range that is at least partially outside the first wavelength range, comprising the steps of directing light in the first wavelength range at the carpet material, and optically examining the moving carpet material at a plurality of predetermined locations relative to its path of movement to detect the presence or absence of the fiducial markings at the predetermined locations, and providing output based on the presence or absence of the fiducial markings at the predetermined locations for use in determining the relative position of the pattern of the carpet based on the configuration of the fiducial marking.

13. A method as set forth in claim 12, wherein the carpet material comprises face fiber combined into a primary backing and a secondary backing which is aligned with and then bonded to the primary backing, the face fiber providing the pattern of the carpet and the fiducial markings being provided in the face fiber, and wherein said step of optically examining the moving carpet material is provided before the secondary material is bonded to the primary backing.

14. A method as set forth in claim 12, wherein the carpet material comprises face fiber combined into a primary backing and a secondary backing which is aligned with and then bonded to the primary backing, the face fiber providing the pattern of the carpet and the fiducial markings being provided in the primary backing, and wherein said step of optically examining the moving carpet material is provided after the secondary material is bonded to the primary backing.

15. A method as set forth in claim 12, wherein the fiducial markings extend transverse to the direction of movement of the carpet material.

16. A method as set forth in claim 15, wherein said step of optically examining the moving carpet material comprises optically examining the moving carpet material at an array of locations extending transverse to the direction of movement of the carpet material.

17. A method as set forth in claim 12, wherein the carpet material comprises face fiber combined into a primary backing and a secondary backing which is aligned with and then bonded to the primary backing, the face fiber providing the pattern of the carpet and the fiducial markings being provided in the primary backing, wherein the primary backing has a front side and a back side, and wherein said step of optically examining the carpet material comprises optically examining the carpet material by an excitation beam directed at the back side of the primary backing.

18. A method as set forth in claim 13, wherein the primary backing has a front side and a back side, and wherein said step of optically examining the carpet comprises optically examining the carpet material by an excitation beam directed at the front side of the primary backing.

19. A method as set forth in claim 13, wherein the fiducial markings are provided in the primary backing, the carpet material is moved over a roller, and said step of optically examining the moving carpet material is performed at predetermined locations relative to the roller as the carpet material is moving over the roller.

20. A method as set forth in claim 19, wherein the primary backing has a front side and a back side, the carpet material moves over the roller with the back side in proximity to the roller, and said step of optically examining the carpet material comprises optically examining the carpet material by an excitation beam directed at the front side of the primary backing.

21. A method for detecting a fiducial marking of a carpet material, comprising the steps of providing the carpet material with a fiducial marking comprising at least one pic line provided in the carpet material material, the pic line configured to be related to the pattern of the carpet material, the fiducial marking characterized by the ability to absorb light in a first wavelength range and to fluoresce in a second wavelength that is at least partially outside the first wavelength range, examining the carpet with (a) an excitation source configured to direct light at the material in the first wavelength range, and (b) a detection device configure to optically examine the carpet, to determine whether fluorescence from the fiducial marking which is in the second wavelength range is detected by the detection device, and to detect the configuration of the pic line and provide output relative thereto.

22. A method as set forth in claim 21, wherein a plurality of pic lines are provided in the carpet material, and the step of examining the carpet comprising examining the plurality of pic lines and detecting the configurations of the plurality of pic lines.

23. A method as set forth in claim 21, wherein the step of examining includes examining the pic line to detect a bow configuration in the pic line.

24. A method as set forth in claim 21, wherein the step of examining includes examining the pic line to detect a skew configuration in the pic line.

25. A method as set forth in claim 21, wherein the step of examining includes examining the pic line to detect either a bow or skew configuration in the pic line.

* * * * *